US007584756B2

(12) United States Patent
Zadoyan et al.

(10) Patent No.: US 7,584,756 B2
(45) Date of Patent: Sep. 8, 2009

(54) APPARATUS AND METHOD FOR CORRECTION OF ABERRATIONS IN LASER SYSTEM OPTICS

(75) Inventors: Ruben Zadoyan, Irvine, CA (US); Guy Vern Holland, San Clemente, CA (US); Zolt Bor, San Clemente, CA (US); Marcel Bouvier, Alisoviejo, CA (US)

(73) Assignee: AMO Development, LLC, Santa Ana, CA (US)

( * ) Notice: Subject to any disclaimer, the term of this patent is extended or adjusted under 35 U.S.C. 154(b) by 291 days.

(21) Appl. No.: 10/919,710

(22) Filed: Aug. 17, 2004

(65) Prior Publication Data

US 2006/0084954 A1    Apr. 20, 2006

(51) Int. Cl.
*A61B 19/00* (2006.01)
*A61B 18/20* (2006.01)

(52) U.S. Cl. .................. 128/898; 606/4; 606/12

(58) Field of Classification Search ........... 606/4–6, 606/10–12; 607/88–95; 351/205–212; 128/898
See application file for complete search history.

(56) References Cited

U.S. PATENT DOCUMENTS

| | | | |
|---|---|---|---|
| 4,665,913 A | 5/1987 | L'Esperance | ............... 606/3 |
| 4,669,466 A | 6/1987 | L'Esperance | ............... 606/3 |
| 4,907,586 A | 3/1990 | Bille et al. | ............... 606/5 |
| 4,988,348 A | 1/1991 | Bille | ............... 606/5 |
| 5,383,199 A | 1/1995 | Laudenslager et al. | ....... 372/25 |
| 5,386,827 A * | 2/1995 | Chance et al. | ............. 600/310 |
| 5,474,549 A | 12/1995 | Ortiz et al. | ............... 606/9 |
| 5,713,893 A * | 2/1998 | O'Donnell, Jr. | ............. 606/10 |
| 5,928,221 A * | 7/1999 | Sasnett et al. | ............... 606/5 |
| 5,980,101 A * | 11/1999 | Unternahrer et al. | ........ 374/32 |
| 6,002,706 A * | 12/1999 | Staver et al. | ............... 372/108 |
| 6,110,166 A | 8/2000 | Juhasz | ............... 606/5 |
| 6,195,164 B1 | 2/2001 | Thompson et al. | ....... 356/376 |
| 6,287,299 B1 * | 9/2001 | Sasnett et al. | ............... 606/12 |
| RE37,585 E | 3/2002 | Mourou et al. | ........ 219/121.69 |
| 6,572,606 B2 | 6/2003 | Kliewer et al. | ............... 606/5 |
| 6,610,050 B2 | 8/2003 | Bille | ............... 606/5 |
| 6,626,898 B2 | 9/2003 | Frey et al. | ............... 606/12 |
| 6,666,855 B2 * | 12/2003 | Somani et al. | ............... 606/5 |
| 6,666,857 B2 | 12/2003 | Smith | ............... 606/12 |
| 6,932,807 B1 | 8/2005 | Tomita et al. | ............... 606/10 |
| 2002/0077622 A1 | 6/2002 | Hofer | |
| 2002/0120198 A1 | 8/2002 | Nakamura | |
| 2002/0125230 A1 | 9/2002 | Haight et al. | ........ 219/121.69 |
| 2003/0036751 A1 | 2/2003 | Anderson et al. | ............ 606/9 |
| 2003/0062350 A1 * | 4/2003 | Staver et al. | ........ 219/121.85 |
| 2003/0216719 A1 | 11/2003 | Debenedictis et al. | ........ 606/10 |
| 2004/0147910 A1 | 7/2004 | Fujieda | |
| 2005/0215986 A1 * | 9/2005 | Chernyak et al. | ............... 606/5 |

OTHER PUBLICATIONS

European Search Report European Application No. 05785356, dated Jun. 5, 2008, 7 pages total.

* cited by examiner

*Primary Examiner*—Ahmed M Farah (57) ABSTRACT

The present invention provides a method for minimizing fluence distribution of a laser over a predetermined pattern. In particular, the method is useful for minimizing fluence variance over a predetermined pattern for lasers used in ophthalmic surgery.

36 Claims, 7 Drawing Sheets
(2 of 7 Drawing Sheet(s) Filed in Color)

APPARATUS AND METHOD FOR CORRECTION OF ABERRATIONS IN LASER SYSTEM OPTICS

TECHNICAL FIELD

The present invention relates to a laser beam energy correction method for correcting the variation in fluence distribution on a focal plane due to aberrations in focusing optics, and a laser driving apparatus adopting the laser beam energy correction method. The method and apparatus of the present invention are particularly, but not exclusively, useful for ophthalmic laser surgery procedures.

BACKGROUND OF THE INVENTION

A specific application of the invention is in the use of a photodisruptive laser for defining a resection plane of a corneal layer to create corneal flap in ophthalmic surgical procedures for vision error correction. Vision impairment can occur for many reasons, and be the result of many causes. One common cause for vision impairment results from a defective condition of the eye which occurs when the refractive characteristics of the cornea do not cause parallel rays of light to focus on the retina. When the eye is at rest, and the rays of light focus in front of the retina, the condition is known as myopia (i.e. nearsightedness). On the other hand, when the rays of light focus behind the retina, the condition is known as hypermetropia or hyperopia (i.e. farsightedness). Both myopic and hyperopic conditions result in varying degrees of vision impairment. In most cases the conditions are correctable.

Eyeglasses or contact lenses are commonly used to correct myopic or hyperopic conditions. For various reasons, however, many persons who suffer with these conditions prefer not to wear eyeglasses or contact lenses. Alternative ways to correct these conditions include known surgical procedures for reshaping the cornea in various ways that are effective in changing its refractive characteristics. For example, in U.S. Pat. Nos. 4,665,913 and 4,669,466 to L'Esperance, a laser system is described which photoablates corneal tissue from the anterior surface of the eye. Another procedure is described in U.S. Pat. No. 4,988,348 to Bille, whereby corneal tissue is first removed to correct vision, and then the newly created surface is smoothed.

Rather than remove and reshape portions of the anterior portion of the eye to correct refractive defects, other procedures have been developed using a technique called intrastromal photodisruption for removing internal stromal tissue. An example of such a procedure is described in U.S. Pat. No. 4,907,586 to Bille et al. Another example of a procedure for removing stromal tissue is the procedure described in U.S. Pat. No. 6,110,166 to Juhasz. In this procedure, an anterior corneal layer can be defined by using a laser to create a series of overlapping photodisrupted areas. The surgeon then separates the corneal layer by lifting it, to gain access to the underlying corneal tissue, which is changed through photoablation. The corneal layer is then repositioned on the cornea.

The photodisruption procedure involves removal of tissue in a stroma in a cornea of an eye using pulsed laser beam which is sequentially focused to individual spots at a plurality of locations in the stroma. Each focus spot has a finite volume, rather than being a single point. Further, each spot has a central point at approximately the center of the finite volume. Photodisruption of stromal tissue occurs at each spot where the beam is focused when fluence is above the threshold value and the volume of stromal tissue disrupted at each spot is approximately equal to the volume of the spot. The amount of tissue damage is dependent on how much the fluence exceeds the threshold value An optimal fluence value exists for a given separation between photodisruption spots to achieve the best surgical result. For example, if the fluence is below the optimal value, then it is difficult to lift the flap. If the fluence is above the optimal value, then an excessive amount of gas is produced during the photodisruption process creating opacity in the cornea, thus complicating the next step of vision correction procedure, photoablation. Clinical studies show that noticeable differences in outcomes occur when fluence varies +/−10%. Consequently, it is important to have a uniform distribution of the fluence between photodisruption points.

Such a pulsed laser syste, (which includes the laser and focusing optics), ideally provides an even fluence distribution across the focal plane, thus providing uniform distribution of the photodisruptive effect. However, the laser systems used in these procedures present the problem of providing nonuniform fluence over a focal plane even when set at a constant energy because of variations of the focal spots in the focal plane. Thus, the variance in fluence distribution may be above the optimal value at some points in the focal plane and below the optimal value at other points in the laser focal plane. This, in turn, results in nonuniform distribution of photodisruption in the focal plane. One reason for the fluence variance is that the optic that the laser is focused through, although generally uniform, contains imperfections and small variations resulting in aberrations in the beam. Aberrations generally change the spot size in the focal plane. By correcting energy, the present invention minimizes the fluence variance at each point in the focal plane where the spot size varies because of aberrations in the laser beam.

U.S. Pat. No. 6,287,299 describes a method of monitoring fluence from focus spot to focus spot by directing a portion of the laser beam energy to a fluence monitoring device to provide a picture of fluence distribution over a curved surface in overlaying pattern. Fluence is controlled by controlling the number of pulses irradiating a single point and by overlaying the spots. It is essential for that method to have multiple pulses irradiating the same point in X/Y plane. However, the '299 patent fails to address the issue of correcting fluence variance due to discrepancies in the focusing optics. Furthermore, the method is not useful for single pulse photodisruption in real-time surgical settings and for high numerical aperture focusing optics when the space between the focusing lens and focal plane is very limited.

Herein, the inventors present a method and apparatus for overcoming the disadvantages of the prior art.

BRIEF SUMMARY OF THE INVENTION

An embodiment of the invention is a laser beam energy correction method for correcting fluence distribution of the laser beam through an optic onto a focal plane, said correction method comprising the steps of: determining the fluence distribution of the laser beam energy over a focal plane; and calibrating the laser beam energy for the predetermined pattern based upon the fluence distribution.

In a specific embodiment, the step of determining the fluence distribution comprises the steps of: focusing the laser beam through an optic into fluence sensitive material positioned in the focal plane; pulsing said laser beam through the optic onto the focal plane; optically damaging the fluence sensitive material; creating fluence sensitive plasma light; measuring the plasma light intensity distribution over the focal plane; and storing the fluence distribution of the focal plane into a computer memory. In one embodiment of the invention, the pulsing comprises a constant energy. In one embodiment of the invention, the pulsing comprises a constant energy of at least about 5,000 pulses per second.

In a specific embodiment, the step of determining the fluence distribution further comprises repeating the focusing, pulsing, measuring and storing steps.

In one embodiment of the invention, measuring fluence distribution comprises capturing a plasma light image with a photodetector.

In one embodiment of the invention, measuring fluence distribution comprises measuring the fluence at a plurality of coordinate points on the focal plane. In a specific embodiment, the plurality of coordinate points comprises at least 1000 points.

In one embodiment of the invention, calibrating the laser beam energy for the predetermined pattern comprises retrieving the stored fluence distribution over the focal plane from the computer memory and modifying the laser beam energy at individual points in the predetermined pattern.

In one embodiment of the invention, the calibrating comprises comparing the stored fluence distribution at points in the predetermined pattern with reference values. In a specific embodiment, the calibrating the laser beam energy for the predetermined pattern comprises minimizing the fluence variance over the predetermined pattern. In a specific embodiment, the calibrating the laser beam energy for the predetermined pattern comprises controlling the energy output of the laser beam through a feedback control mechanism.

In one embodiment of the invention, the focal plane comprises a substantially flat surface. In an embodiment of the invention, the predetermined pattern comprises a spiral.

One embodiment of the present invention is an apparatus for performing the method described herein, comprising a laser source, a focusing mechanism, an electro-optic modulator, and a computer-controlled driver for said EO modulator. It is contemplated that the computer-controlled driver may include an appropriate software program for analyzing the measured fluence distribution data, and calibrating the laser beam energy as a result of the analysis. The apparatus may also include a fluence sensitive image and a feedback mechanism.

One embodiment of the present invention is a laser beam energy correction method for correcting fluence distribution of the laser beam over a predetermined pattern on an object, said correction method comprising the steps of: determining the fluence distribution over a focal plane, said focal plane comprising a fluence sensitive image of plasma light distribution; calibrating the laser beam energy over the predetermined pattern; focusing the laser beam on the object; and pulsing the adjusted laser beam over the predetermined pattern on the object.

BRIEF DESCRIPTION OF THE DRAWINGS

The patent or application file contains at least one drawing executed in color. Copies of this patent or patent application publication with color drawing(s) will be provided by the Office upon request and payment of the necessary fee. For a more complete understanding of the present invention, reference is now made to the following descriptions taken in conjunction with the accompanying drawing, in which.

DETAILED DESCRIPTION OF THE INVENTION

Figure 1:
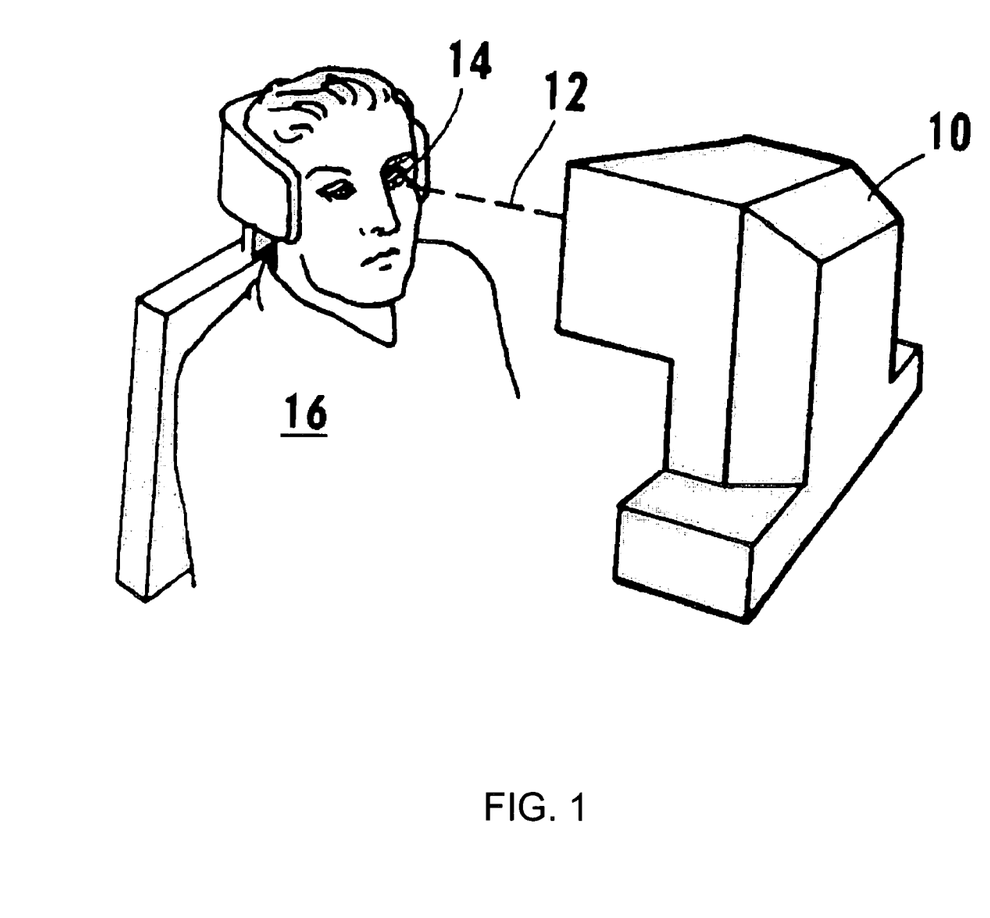
FIG. 1 is a perspective view of a patient being treated with the method of the present invention.
Figure 2:
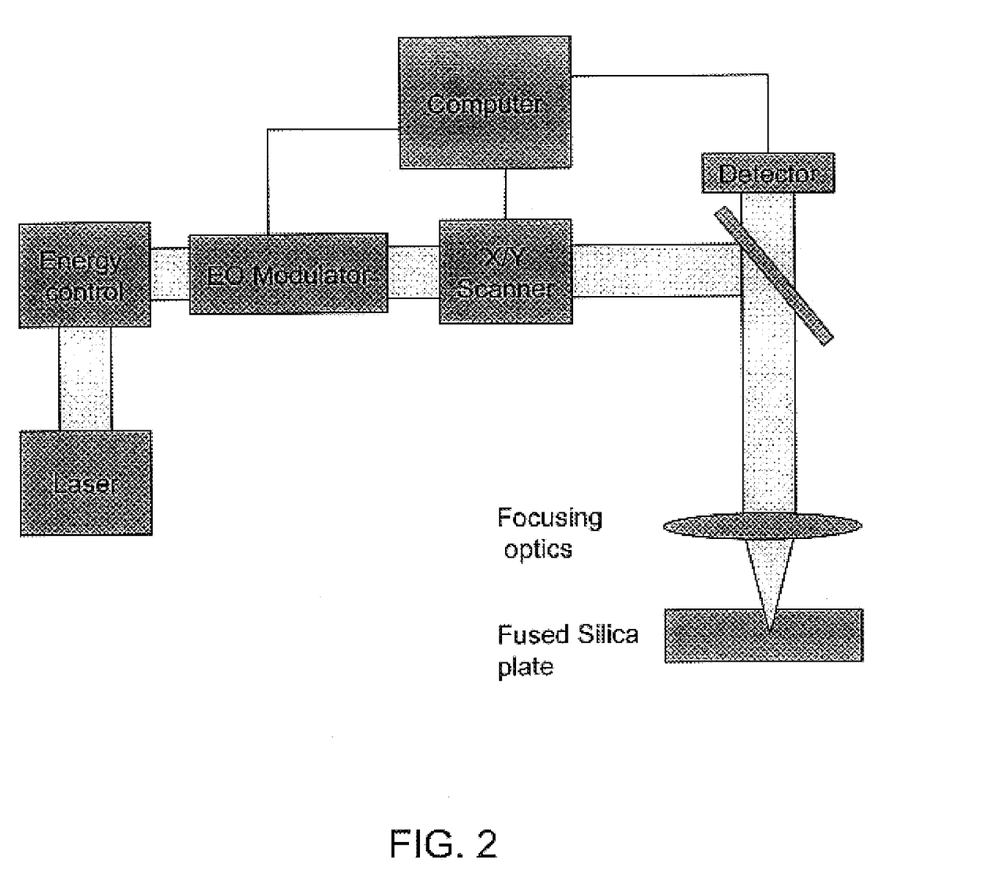
FIG. 2 is a block diagram of the laser system utilizing the method of the present invention.
Figure 3:
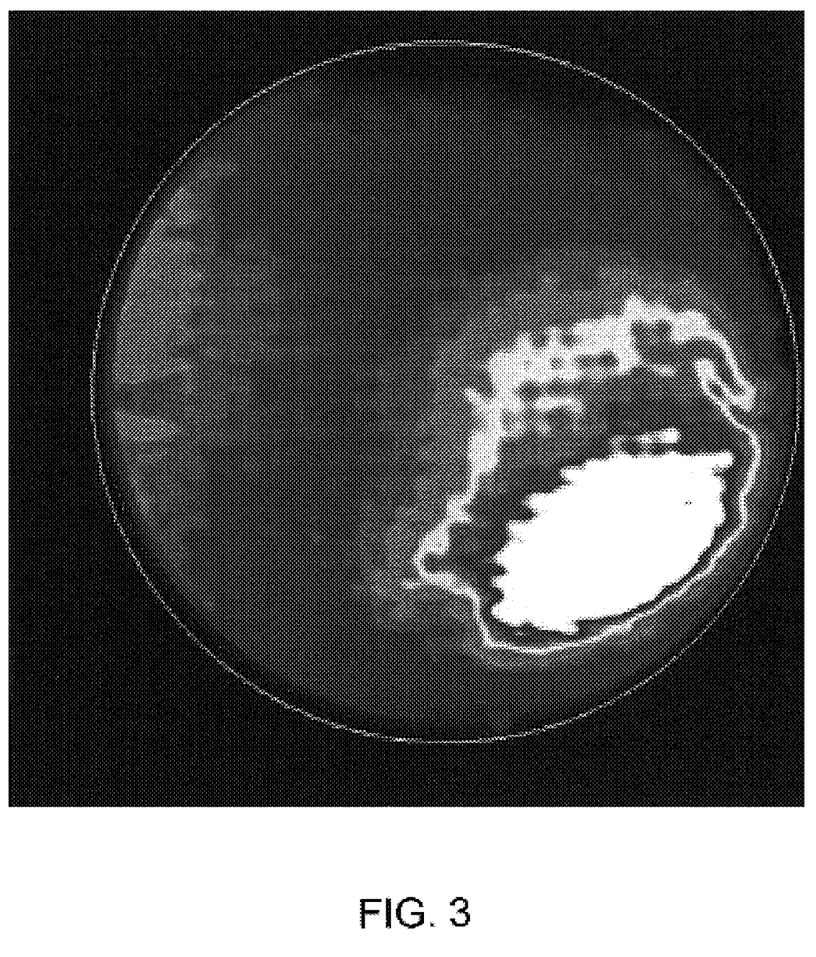
FIG. 3 is an exemplary photoablation response fluence distribution showing uneven fluence distribution across the focal plane.
Figure 4:
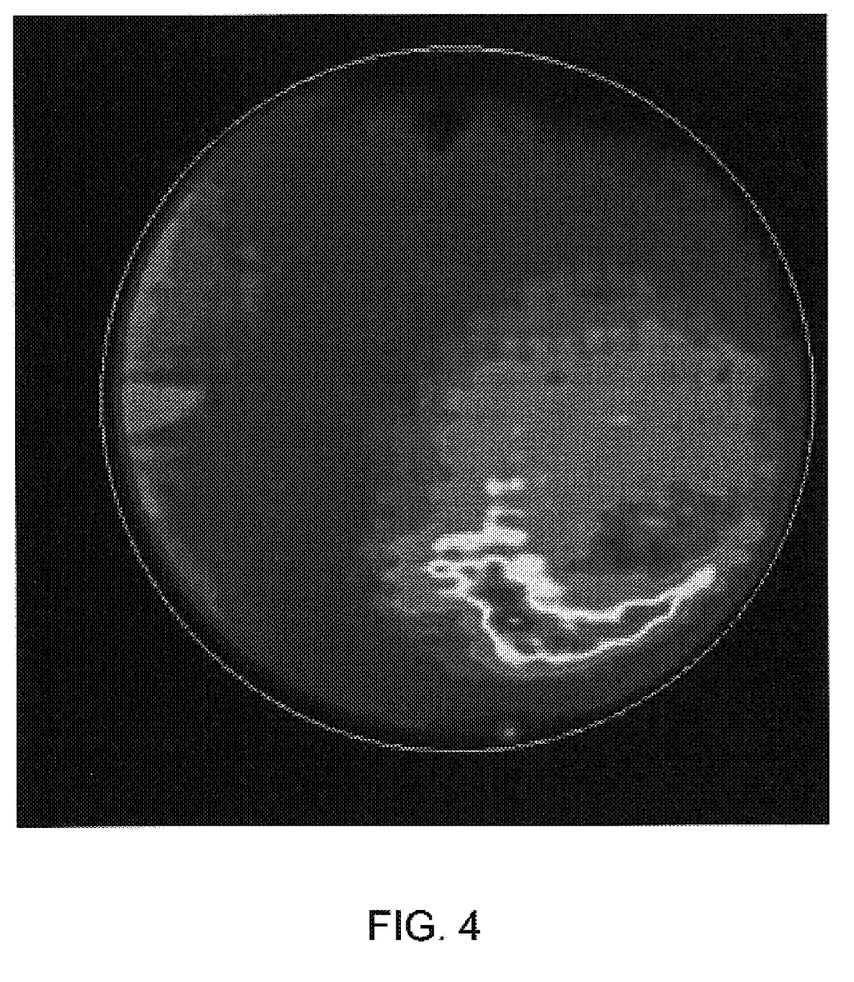
FIG. 4 shows the difference in fluence distribution when the feedback mechanism is activated.
Figure 5:
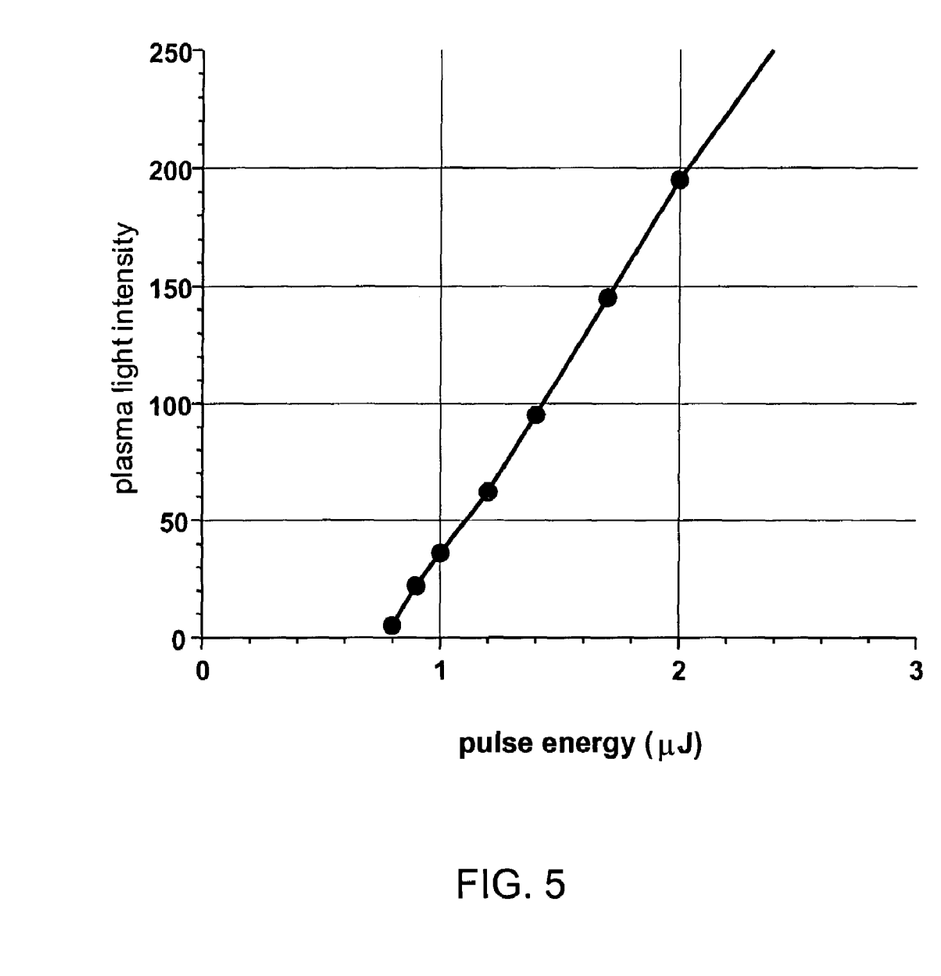
FIG. 5 shows the plasma light intensity dependence on laser pulse energy in fused silica sample at a typical spot size of 2.5 μm.

Referring initially to FIG. 1, depicting a prior art image, an apparatus 10 for generating a laser beam 12 is shown. The laser beam 12 is directed onto an eye 14 of a patient 16. For purposes of the present invention, the apparatus 10 is capable of generating a pulsed laser beam 12 having physical characteristics similar to those of the laser beams generated by a laser system as disclosed and claimed in U.S. Pat. No. 4,764,930, which is exclusively licensed to the assignee of the present invention. Various laser sources may be used with the inventive system and method, including infrared, visible, and UV lasers. Further, laser sources to be used with the inventive system may be continuous wave, Q-switched pulse, and mode-locked ultrashort pulse lasers. Although the following is not an exhaustive list, lasers of the foregoing type may be used with the present invention.

In one embodiment, the present invention contemplates the use of a pulsed laser beam 12 which has pulses with durations as long as a few nanoseconds or as short as only a few femtoseconds.

In one embodiment, a laser unit is controlled by software for photodisruption of the cornea utilizing a laser beam of constant energy, composed of an optical train of pulses with a duration of approximately 600 femtoseconds at a repetition rate of up to several hundred thousand Hz.

The optical delivery system determines a 3-dimensional position in the patient's cornea at which the laser is focused. When the laser is pulsed, the energy delivered to the point of focus is sufficient to ionize tissue (photodisrupt) in a very small volume. Repetitively setting a focus point and pulsing the laser results in a resected plane of tissue.

In one embodiment of the invention, the method is useful for use in real-time, such that the information needed to correct the fluence variance of a ophthalmic surgery laser as described in the present invention is stored in a computer memory and can be instantly retrieved prior to surgery. It is contemplated that the fluence variance of the laser beam can thus be corrected during ophthalmic surgery. One with skill in the art understands the fluence, or energy density, is the irradiance multiplied by the exposure time, and is commonly measured in Joules/square centimeter. In another embodiment, the laser is pulsed onto a focal plane prior to surgery. The fluence distribution over a predetermined pattern is determined, and the laser beam energy is calibrated such that the laser fluence variance is minimized between focal spots over the predetermined pattern. The calibrated laser is then focused through an applanation lens during surgery. In another embodiment of the invention, the laser is calibrated over a predetermined pattern based on stored fluence variance data that is in a computer memory, and thus the laser does not have to be recalibrated prior to every surgery.

In one embodiment of the invention, the reference focal plane comprises a plurality of coordinate points on an X/Y axis. In certain embodiments of the invention, the laser is focused at a specific Z coordinate inside the aplanation lens preferably made of fused silica over a plurality of spots on the X/Y axis. The laser is pulsed onto the focal plane at energy above the optical breakdown threshold in fused silica. Plasma light, which is proportional to fluence, is created at each point and its intensity is measured. Distribution of plasma light intensity over different X/Y coordinates is representative of fluence variance in the focal plane. The fluence data is then stored in a computer memory. The laser energy is adjusted such that the calibrated fluence variance over the predetermined path is minimized. One with skill in the art realizes that at certain coordinate points, the laser beam energy must be either increased or decreased in order to calibrate the laser beam so that the fluence variance is minimized over a predetermined pattern. In a specific embodiment, it is contemplated that when the variance of the fluence is over a predefined range, then the laser beam energy will be corrected such that the fluence variance is minimized. In certain embodiments of the invention, the predefined range is set for a fluence variance at a particular coordinate point greater than 5-10% variance from the desired fluence, greater than 10-15% variance from the desired fluence, greater than 15-20% variance from the desired fluence, greater than 20-25% variance from the desired fluence, greater than 25-30% variance from the desired fluence, greater than 30-35% variance from the desired fluence, greater than 35-40% variance from the desired fluence, greater than 40-45% variance from the desired fluence, or greater than 45-50% variance from the desired fluence.

It is contemplated that in a specific embodiment, the laser beam will be calibrated at a particular Z coordinate point in the X/Y axis, and that the laser can then be adjusted to focus on a different Z coordinate for surgery. However, the invention is not limited to calibration at a single Z coordinate.

In an embodiment of the invention, the step of determining the fluence distribution over a focal plane is accomplished by determining the fluence at a plurality of spots on the focal plane. In a specific embodiment, the focal plane is about 10 mm in diameter. The spot separation is about 10 microns in a specific embodiment.

In another embodiment of the invention, a reference library of fluence measurements is stored in a computer memory corresponding to particular predetermined paths. It is contemplated that the reference library may comprise information that can be customized depending on the procedure for which the laser is utilized.

In one embodiment of the invention, the reference focal plane is substantially flat. In other embodiments of the invention, it is contemplated that the reference focal plane is curved.

It is contemplated that the predetermined patterns useful for the present invention include, but are not limited to, a circle, an oval, a raster, a spiral, or any combination thereof.

Further, the present invention recognizes that internal tissue "photodisruption," can be effectively accomplished using a pulsed laser energy if the irradiance of the beam, its focal spot size, and the proper layering of photodisruption sites are effectively controlled. Accordingly, it is an object of the present invention to provide an improved method for performing intrastromal photodisruption on the cornea of an eye by providing a method for correcting fluence distribution in a focal plane of the laser beam.

The physical characteristics of the laser beam, as well as the manner of focusing the laser beam, are important to the proper performance of the method of the present invention. As indicated above, these considerations are interrelated. Insofar as the characteristics of the laser beam are concerned, several factors are important. The laser beam should have a wavelength that allows the light to pass through the cornea without absorption by the corneal tissue. Generally, the wavelength should be in the range of 0.4-1.9 micrometers with a wavelength of approximately 1054 nm being preferred. The irradiance of the beam for accomplishment of photodisruption of stromal tissue at the focal spot should be greater than the threshold for optical breakdown of the tissue. Preferably, the irradiance should not be more than ten (10) times greater than the threshold for optical breakdown.

The spot size of the focused laser beam should be small enough to achieve optical breakdown of stromal tissue at the focal spot. Typically, this requires the spot size to be approximately 1.2 microns-10 microns in diameter. Additionally, it is preferable that the spot configuration be as close to circular as possible.

The applanation lens as described herein may be glass, fused silica, or medical grade plastic.

I. Measuring Fluence Distribution

The threshold fluence plate, as described herein, is a means for measuring fluence distribution. The principle of operation is based on generating plasma light while optically damaging the sample, which, in certain embodiments, is a fused silica plate. The laser beam is focused inside the bulk of the plate to avoid contribution from surface. At a given pulse duration the optical damage of a material depends on threshold value defined as fluence—energy per unit area. High density plasma created in the process of optical damage emits visible light. Intensity depends on fluence value above the threshold. If the spot size of the beam is constant then the amount of emitted light depends on energy. In the range of 1-3 uJ (typical range of energy for surgery) the dependence is linear. Plasma light is proportional to energy, or fluence. A signal is collected by a photodetector. In practice, the signal is collected the following way: the scanner scans the beam over the focal plane located inside the sample. For each point, a computer records the position of the beam on X/Y plane and the intensity of plasma light measured with a built-in video camera. The beam moves over the predetermined pattern and plasma light distribution in the focal plane is recorded. Since the energy is constant, the variations in plasma light intensity are due to spot size variations. The image is stored in the computer for comparison.

II. Calibrating the Fluence Variance

Figure 6:
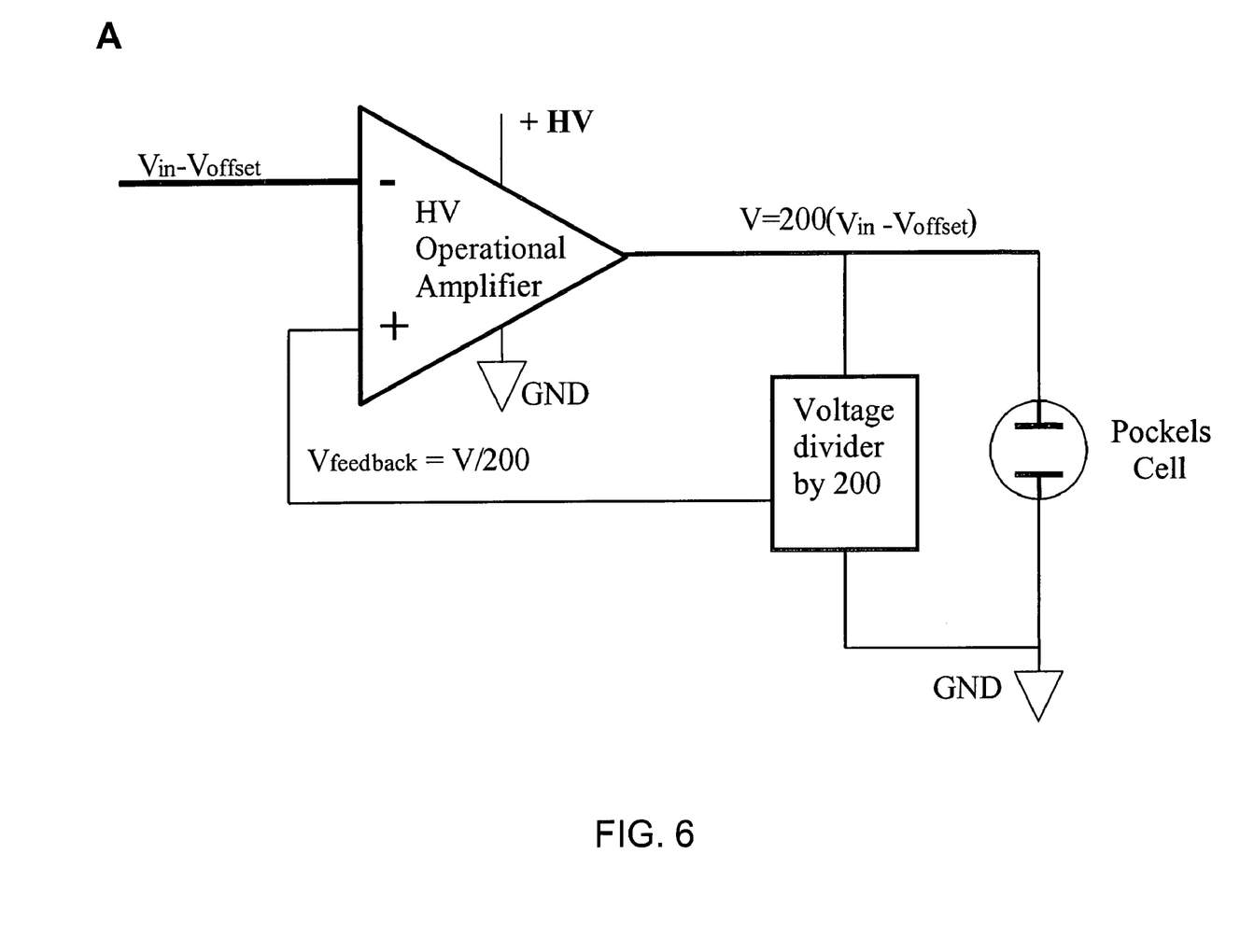
FIG. 6 shows the block diagram and schematics of the high voltage linear amplifier controlling the electro-optic modulator.

For example, in certain embodiments, it is contemplated that the user will choose a signal level on the fluence distribution image (reference) around which to minimize fluence distribution. During the procedure at each coordinate point on the X/Y plane, the computer compares the reference value with the actual signal value. Depending on the sign of the difference (i.e., positive or negative) and the magnitude of the difference, the energy is increased or decreased to minimize the fluence distribution. Energy adjustment in real time is accomplished by an electro-optic (EO) modulator. Transmission of light through the EO modulator is governed by feedback voltage controlled by the computer. Feedback control mechanisms for EO modulators are familiar to one with skill in the art. Intensity of light transmitted through an electro optic modulator, in this case Pockels cell placed between two crossed polarizes, is given by:

$$E_{out} = E_{in}\sin^2\left(V\frac{\pi}{2V_{\lambda/2}}\right)$$

where V is the applied voltage, $V_{\lambda/2}$ is half wave voltage, $E_{in}$ and $E_{out}$ are intensities at the input and output of the modulator. Initial transmission of the modulator is chosen at 50% by applying DC offset voltage of $V_{offset}=V_{\lambda/2}/2$ from the computer. In the range of transmissions from 30% to 70% the dependence on voltage is close to be linear. High voltage linear amplifier is used to provide feedback and to control transmission of the modulator. Block diagram of the feedback loop along with the detailed schematics are shown in FIGS. 6A & 6B. $V_{in}$ is the voltage generated by the computer to control the transmission of the modulator. Depending on the sign and amplitude of the $V_{in}$-$V_{offset}$ the total transmission of the modulator can be varied between 30-70% for each pulse, thus controlling the fluence in the focal plane.

In a preferred embodiment, the present invention is directed towards lasers used in the field of laser vision correction surgery. However, the scope of the invention is not limited thereto. It is contemplated that the method and apparatus of the present invention will be useful in other fields in which it is desirable to have an even distribution of fluence across a focal plane, or laser beam spot.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A laser beam energy correction method for correcting fluence distribution of the laser beam over a predetermined scan pattern for a target, said correction method comprising the steps of:
    determining the fluence distribution of the laser beam energy over a focal plane within the target, wherein said determining the fluence distribution comprises the steps of:
        focusing the laser beam through an optic to the focal plane;
        pulsing said laser beam through the optic onto the focal plane;
        measuring the fluence distribution over the focal plane; and
        storing the fluence distribution of the focal plane into a computer memory; and
    calibrating the laser beam by modifying the laser beam energy for the predetermined scan pattern based upon the fluence distribution.

2. The method of claim 1, further comprising repeating the focusing, pulsing, measuring and storing steps.

3. The method of claim 1, wherein fluence sensitive material is positioned within the focal plane.

4. The method of claim 1, wherein measuring fluence distribution comprises capturing a signal with a photodetector.

5. The method of claim 4, wherein the signal comprises plasma light.

6. The method of claim 1, wherein measuring fluence distribution comprises measuring the fluence at a plurality of coordinate points on the focal plane.

7. The method of clam 6, wherein the plurality of coordinate points comprises at least 1000 points.

8. The method of claim 1, wherein the pulsing comprises a constant energy.

9. The method of claim 1, wherein the pulsing comprises at least about 1,000 pulses per second.

10. The method of claim 1, wherein calibrating the laser beam energy for the predetermined pattern comprises retrieving the stored fluence distribution over the focal plane from the computer memory and modifying the laser beam energy at individual points in the predetermined pattern.

11. The method of claim 10, wherein calibrating comprises comparing the stored fluence distribution at points in the predetermined pattern with reference values.

12. The method of claim 1, wherein calibrating the laser beam energy for the predetermined pattern comprises minimizing the fluence variance over the predetermined pattern.

13. The method of claim 1, wherein the focal plane comprises a substantially flat surface.

14. The method of claim 1, wherein predetermined pattern comprises a spiral.

15. A laser beam energy correction method for correcting fluence distribution of the laser beam over a predetermined scan pattern for a target, said correction method comprising the steps of:
    determining the fluence distribution of the laser beam energy over a focal plane within the target;
    calibrating the laser beam by modifying the laser beam energy for the predetermined scan pattern based upon the fluence distribution by controlling the energy output of the laser beam through a feedback control mechanism.

16. A laser beam energy correction method for correcting fluence distribution of the laser beam over a predetermined pattern on an object, said correction method comprising the steps of:
    calibrating the laser beam energy over the predetermined pattern;
    focusing the laser beam on the object; and
    pulsing the adjusted laser beam over the predetermined pattern on the object;
    wherein calibrating the laser beam energy over the predetermined pattern comprises retrieving a stored fluence distribution over the predetermined pattern from a computer memory and modifying the laser beam energy at individual points in the predetermined pattern.

17. The method of claim 16, wherein calibrating the laser beam energy over the predetermined pattern comprises controlling the energy output of the laser beam through a feedback control mechanism.

18. The method of claim 16, wherein said calibrating comprises the steps of:
focusing the laser beam through an optic to a focal plane;
pulsing said laser beam through the optic onto the focal plane; and
measuring the fluence distribution over the focal plane;
storing the fluence distribution of the focal plane into the computer memory.

19. The method of claim 18, further comprising repeating the focusing, pulsing, measuring and storing steps.

20. The method of claim 18, wherein fluence sensitive material is positioned within the focal plane.

21. The method of claim 18, wherein measuring fluence distribution comprises capturing a signal with a photodetector.

22. The method of claim 21, wherein the signal comprises plasma light.

23. The method of claim 18, wherein measuring fluence distribution comprises measuring the fluence at a plurality of coordinate points on the focal plane.

24. The method of claim 23, wherein the plurality of coordinate points comprises at least 1000 points.

25. The method of claim 18, wherein the pulsing comprises a constant energy.

26. The method of claim 18, wherein the pulsing comprises at least about 10,000 pulses per second.

27. The method of claim 18, wherein calibrating the laser beam energy over the predetermined pattern comprises minimizing the fluence variance over the predetermined pattern.

28. The method of claim 18, wherein the focal plane comprises a substantially flat surface.

29. The method of claim 18, wherein the optic comprises a glass lens or a medical grade plastic lens.

30. The method of claim 18, wherein the focal plane is a threshold fluence plate.

31. A method of compensating for aberrations in laser system optics, the method comprising:
directing a plurality of laser beam pulses from a laser to a plurality of focal spots in a sample according to a predetermined pattern, each pulse of the pattern being directed to a different focal spot and the pulses of the pattern having a pulse energy which is constant among the pulses;
measuring a fluence distribution across the predetermined pattern;
determining a fluence variance across the predetermined pattern based on the fluence distribution; and
calibrating the laser to emit laser beam pulses having varying pulse energies to reduce the fluence variance.

32. The method of claim 31, wherein measuring the fluence distribution includes detecting plasma light resulting from photodisruption at each focal spot within the sample.

33. The method of claim 31, wherein calibrating the laser includes calibrating the laser to emit laser beam pulses having varying pulse energies which minimize the fluence variance.

34. The method of claim 31, wherein calibrating the laser includes controlling the pulse energies through a feedback control mechanism.

35. The method of claim 31, wherein the predetermined pattern is non-planar.

36. The method of claim 31, wherein the predetermined pattern comprises a spiral pattern.

* * * * *

UNITED STATES PATENT AND TRADEMARK OFFICE
CERTIFICATE OF CORRECTION

PATENT NO.       : 7,584,756 B2                                      Page 1 of 1
APPLICATION NO.  : 10/919710
DATED            : September 8, 2009
INVENTOR(S)      : Zadoyan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 608 days.

Signed and Sealed this

Fourteenth Day of September, 2010

David J. Kappos
*Director of the United States Patent and Trademark Office*